United States Patent  
Allenic et al.

(10) Patent No.: US 8,603,839 B2  
(45) Date of Patent: Dec. 10, 2013

(54) IN-LINE METROLOGY SYSTEM

(75) Inventors: Arnold Allenic, Arbor, MI (US);
Stephan Paul George, II, Perrysburg, OH (US); Sreenivas Jayaraman, Holland, OH (US); Oleh Karpenko, Perrysburg, OH (US); Chong Lim, Perrysburg, OH (US)

(73) Assignee: First Solar, Inc., Perrysburg, OH (US)

( * ) Notice: Subject to any disclaimer, the term of this patent is extended or adjusted under 35 U.S.C. 154(b) by 133 days.

(21) Appl. No.: 13/189,913

(22) Filed: Jul. 25, 2011

(65) Prior Publication Data  
US 2012/0021539 A1  Jan. 26, 2012

Related U.S. Application Data

(60) Provisional application No. 61/367,126, filed on Jul. 23, 2010.

(51) Int. Cl.  
*H01L 21/02* (2006.01)

(52) U.S. Cl.  
USPC .......... 438/16; 438/15; 438/17; 257/E21.529; 257/E31.052

(58) Field of Classification Search  
USPC ................ 438/16; 257/E21.529, 31.052  
See application file for complete search history.

(56) References Cited

U.S. PATENT DOCUMENTS

| 5,270,222 A | 12/1993 | Moslehi |
| 5,386,119 A | 1/1995 | Ledger |
| 5,416,594 A | 5/1995 | Gross et al. |
| 5,555,474 A | 9/1996 | Ledger |
| 5,764,365 A | 6/1998 | Finarov |
| 5,856,871 A | 1/1999 | Cabib et al. |
| 5,936,726 A | 8/1999 | Takeda et al. |
| 6,048,742 A | 4/2000 | Weyburne et al. |
| 6,383,824 B1 | 5/2002 | Lensing |
| 6,563,578 B2 | 5/2003 | Halliyal et al. |
| 6,791,680 B1 | 9/2004 | Rosengaus et al. |
| 6,946,394 B2 | 9/2005 | Fielden et al. |
| 7,002,689 B2 | 2/2006 | Liu et al. |
| 7,046,375 B2 | 5/2006 | Bischoff et al. |
| 7,049,156 B2 | 5/2006 | Kueny |
| 7,130,029 B2 | 10/2006 | Wack et al. |
| 7,139,083 B2 | 11/2006 | Fielden et al. |
| 7,271,921 B2 | 9/2007 | Shortt |
| 7,301,149 B2 | 11/2007 | Mackin et al. |
| 7,324,193 B2 | 1/2008 | Lally et al. |

(Continued)

FOREIGN PATENT DOCUMENTS

| DE | 19635072 | 3/1998 |
| JP | 11003923 | 1/1999 |
| WO | WO 01/07881 A1 | 2/2001 |
| WO | WO 2009/143921 A1 | 12/2009 |

OTHER PUBLICATIONS

Bin Fan et al., "In situ optical monitor system for CIGS solar cell applications", Chinese Optics Letters, Apr. 30, 2010, pp. 186-188, vol. 8.

(Continued)

*Primary Examiner* — Michael Lebentritt  
(74) *Attorney, Agent, or Firm* — Dickstein Shapiro LLP

(57) ABSTRACT

A metrology system for gauging and spatially mapping a semiconductor material on a substrate can be used in controlling deposition and thermal activation processes.

24 Claims, 10 Drawing Sheets

(56) References Cited

U.S. PATENT DOCUMENTS

| | | |
|---|---|---|
| 7,327,444 B2 | 2/2008 | Naka et al. |
| 7,414,721 B1 | 8/2008 | Suvkhanov et al. |
| 7,433,056 B1 | 10/2008 | Janik |
| 7,505,133 B1 | 3/2009 | Zawaideh et al. |
| 7,526,354 B2 | 4/2009 | Madriaga et al. |
| 7,567,344 B2 * | 7/2009 | LeBlanc et al. ............ 356/239.1 |
| 7,639,351 B2 | 12/2009 | Chen et al. |
| 7,667,858 B2 | 2/2010 | Chard et al. |
| 7,831,528 B2 | 11/2010 | Doddi et al. |
| 7,940,383 B2 | 5/2011 | Noguchi et al. |
| 7,948,631 B2 | 5/2011 | Walsh |
| 7,948,636 B2 | 5/2011 | De Groot |
| 2005/0275850 A1 | 12/2005 | Bischoff |
| 2007/0232065 A1 | 10/2007 | Basol |
| 2009/0051914 A1 | 2/2009 | Trupke et al. |
| 2009/0218314 A1 | 9/2009 | Davis |
| 2010/0195096 A1 * | 8/2010 | Schlezinger ............... 356/237.5 |
| 2010/0197051 A1 * | 8/2010 | Schlezinger et al. ........... 438/16 |
| 2010/0271621 A1 | 10/2010 | Levy et al. |
| 2011/0025839 A1 | 2/2011 | Trupke et al. |
| 2011/0033957 A1 * | 2/2011 | Holden et al. .................. 438/16 |
| 2011/0117681 A1 | 5/2011 | Bardos et al. |
| 2012/0176146 A1 * | 7/2012 | Oborina et al. ............... 324/658 |
| 2013/0029396 A1 * | 1/2013 | Choi et al. .................... 435/174 |

OTHER PUBLICATIONS

Roland Scheer et al., "Advanced diagnostic and control methods of processes and layers in CIGS solar cells and modules", Progress in Photovoltaics: Research and Applications, 2010, pp. 467-480, vol. 18.

S.J.C. Irvine et al., "In situ monitoring of the MOCVD growth of CdS/CdTe", Journal of Crystal Growth, 2000, pp. 117-123, vol. 221.

* cited by examiner (A)

(B)

IN-LINE METROLOGY SYSTEM

This application claims priority under 35 U.S.C. §119(e) to Provisional Application No. 61/367,126, filed on Jul. 23, 2010; which is incorporated herein by reference.

TECHNICAL FIELD

This invention relates to a metrology system for gauging a semiconductor material on a substrate.

BACKGROUND

Ellipsometer and spectrophotometers are available to predict semiconductor film thickness. Similar tools can measure semiconductor band-gap based on the absorption of incident light or through measurements of the diffuse reflectance of the semiconductor. A system having greater functionality than known systems is desirable.

DETAILED DESCRIPTION

Figure 1:
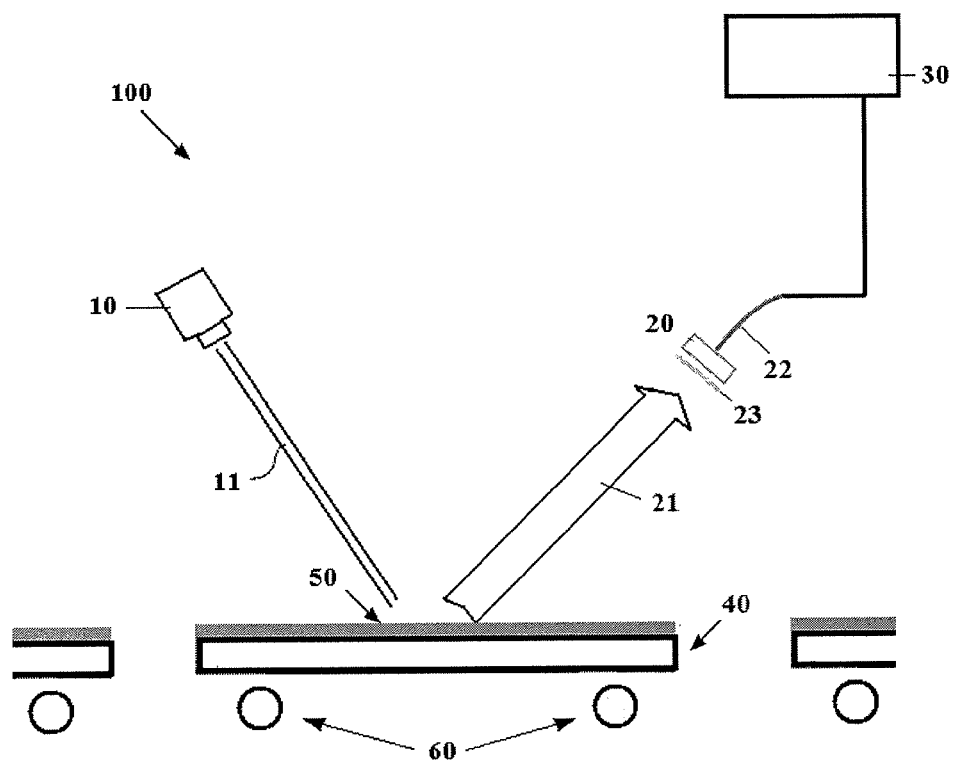
FIG. 1 is a diagram illustrating a metrology system.

Photovoltaic devices can include multiple layers created on a substrate (or superstrate). For example, a photovoltaic device can include a barrier layer, a transparent conductive oxide (TCO) layer, a buffer layer, and a semiconductor layer formed in a stack on a substrate. Each layer may in turn include more than one layer or film. For example, the semiconductor layer can include a first film including a semiconductor window layer, such as a cadmium sulfide layer, formed on the buffer layer and a second film including a semiconductor absorber layer, such as a cadmium telluride layer formed on the semiconductor window layer. Additionally, each layer can cover all or a portion of the device and/or all or a portion of the layer or substrate underlying the layer. For example, a "layer" can include any amount of any material that contacts all or a portion of a surface.

Semiconductor band-gap can be measured based on the absorption of incident light or through measurements of the diffuse reflectance of the semiconductor. The available tools include spectrophotometers, ellipsometers and quantum efficiency measurement device. These devices characterize the optical property of the material being measured. There are some measurement devices for monitoring and controlling semiconductor film deposition and annealing processes thin film photovoltaic manufacturing; these include vacuum pressure gauges, thermocouples and advanced electronic controls systems for automated processing. However, there is no unified measurement system that can predict the end-of-line performance of a semiconductor device based on a combination of inputs including the measured optical properties and state of process variables.

A metrology system and related method for gauging a semiconductor material are developed. The system can measure the optical properties of the device that are a consequence of a certain operating levels of process-variables in semiconductor device (e.g. photovoltaic) manufacturing process. The optical information thus obtained along with process information can be used to control device structure (electrical doping, junction formation) and eventually device performance.

In one aspect, a metrology system for gauging a semiconductor material on a substrate during a semiconductor film deposition and anneal process can include an optical source for generating an optical radiation to illuminate a portion of the semiconductor material, a sensor for measuring the absorption, or reflection of the optical radiation in the semiconductor material, and a processing module for analyzing the sensor measurement to obtain the information including but not limited to band gap or absorption band-edge, thickness of the semiconductor material, and even surface roughness. The processing module can provide an estimation of device performance based on the sensor measurement.

The metrology system can include a spectrophotometer. The metrology system can include an ellipsometer. The metrology system can include a quantum efficiency measurement setup. The optical signal incident on the semiconductor material can be converted to electrical signals to gauge the quantum efficiency of the semiconductor material. The semiconductor material can include cadmium telluride. The semiconductor material can include cadmium sulfide. The semiconductor material can include a mixed layer containing varying proportions of both cadmium telluride and cadmium sulfide. The metrology system may involve the use of an optical source that generates the probe beam that is incident on the sample being measured. The metrology system can include an optical assembly to collect diffuse or specular reflection from the substrate. The metrology system can include an optical assembly to collect the light transmitted through the semiconductor. The sensor may include a spectrometer to parse the light into component wavelengths. The sensor may include a photodiode or a photo-multiplier to convert the optical signal to electrical signals for processing. The semiconductor material can include a bilayer of semiconductor material. The substrate can be transported on a conveyor. the metrology system is configured to measure the semiconductor material when the substrate is in motion. The system can adjust the semiconductor film deposition and anneal process when it drifts from its purported baseline by a feed-back control loop.

In another aspect, a method of gauging a semiconductor material on a substrate during a semiconductor film deposition and anneal process can include generating an optical radiation to illuminate a portion of the semiconductor material, measuring the absorption, or reflectance of the optical radiation from the semiconductor material, and analyzing the measurement data to obtain the information on the optical band gap, or absorption edge, thickness and surface roughness of the semiconductor material. The method can include transporting the substrate on a conveyor. The method can include measuring the quantum efficiency of the semiconductor material. The method can include measuring the refractive index of the semiconductor material. The method can include correlating the optical properties to quantify the physical changes in the material like inter-diffusion of the semiconductor layers. The semiconductor material can include cadmium telluride. The semiconductor material can include cadmium sulfide. The semiconductor material can include a mixed layer containing varying proportions of both cadmium telluride and cadmium sulfide. The method can include estimating of device performance based on the sensor measurement and the concomitant prediction of changes in the material properties. The method can include adjusting the semiconductor film deposition and anneal process when it drifts from its purported baseline with a feed-back control loop.

In another aspect, a method of manufacturing a photovoltaic device gauging and spatially mapping a semiconductor material on a substrate during a semiconductor film deposition and anneal process can include transporting a substrate on a conveyor, depositing a semiconductor material on the substrate, annealing the semiconductor material on the substrate, generating an optical radiation to illuminate a portion of the semiconductor material, measuring the optical property of the semiconductor material, and analyzing the measurement data to obtain the information on the band gap, thickness and surface roughness of the semiconductor material. The method can include measuring the refractive index of the semiconductor material. The method can include estimating of device performance based on the sensor measurement and a predictive model. The method can include measuring the impurity percentage in the semiconductor material. The semiconductor material can include an inter-diffused bilayer of semiconductor materials. The method can include adjusting the semiconductor material deposition and anneal process when it drifts from its purported baseline with a feed-back control loop. The method can include adjusting the measured location of the semiconductor material for spatially mapping a semiconductor material. The method can include utilizing the band-gap measured in the semiconductor material to control electrical junction formation of a semiconductor device and affect the performance of the semiconductor device.

The metrology system can correlate the specific process variables in the semiconductor device (e.g. photovoltaic module) manufacturing process to the optical properties of the device. Thereby, the metrology system can utilize the band-gap measurement result in the specific semiconductor device to control junction formation and affect device performance. For example, a metrology system can measure the precise band-gap in an area of interest and directly correlates the same to the semiconductor deposition and diffusion anneal process of a cadmium telluride (CdTe) photovoltaic device manufacturing where the junction is defined. The metrology system can also estimate the specific layer thickness that make up the device. Furthermore, using a feed-back control loop, the metrology system can adjust the process when it drifts from its purported baseline. The metrology system can also provide an estimation of device performance based on the measured metrics.

Referring to FIG. 1, metrology system 100 can include optical source 10 for generating optical radiation 11 to illuminate a portion of semiconductor material 50 on substrate 40. Metrology system 100 can include sensor 20 for measuring the optical property of semiconductor material 50. Filter 23 can be positioned in front of sensor 20 to control the detected wavelength spectrum of incoming radiation 21. Cable 22 can be included to communicate the measurement result to processing module 30 to obtain the information of the band gap and thickness of semiconductor material 50. Substrate 40 can be transported on conveyor 60. Metrology system 100 can provide measurements for thin film metrology.

In some embodiments, filter 23 can be not included in metrology system 100. In other embodiments, filter 23 can be positioned at the output side of optical source 10. Optical source 10 can be positioned at an angle ranging from 2 degree-90 degree with respect to substrate normal. Similarly sensor 20 can be positioned at an angle 2 degree-90 degree with respect to substrate normal. The system 100 can be in an enclosure to prevent ambient light from disrupting measurement. There can be attachments like a photo-eye that detects the presence of a panel to start the measurement. Another attachment can be an infra-red pyrometer to measure the substrate temperature. Temperature information is essential to normalize any optical data that is being measured as material properties change with temperature. Optical source 10 and sensor 20 can be on mounted on translating mounts and motorized to map the substrate. There may be more than one pair of 10-20 measuring simultaneously.

With a reflection measurement set-up shown in FIG. 1, metrology system 100 can include at least one polarizer to implement ellipsometry technique for the investigation of the dielectric properties (complex refractive index or dielectric function) of thin films. Upon the analysis of the change of polarization of light, which is reflected off a sample portion of semiconductor material 50, processing module 30 can yield information about layers in semiconductor material 50 that are thinner than the wavelength of the probing light itself, even down to a single atomic layer. Metrology system 100 can probe the complex refractive index or dielectric function tensor, which gives information of fundamental physical parameters of semiconductor material 50 and can be related to a variety of sample properties, including morphology, crystal quality, chemical composition and spatial variations of the same, electrical conductivity, optical band-gap and surface topography. It can be used to characterize film thickness for single layers or complex multilayer stacks ranging from a few angstroms or tenths of a nanometer to several micrometers.

Figure 2:
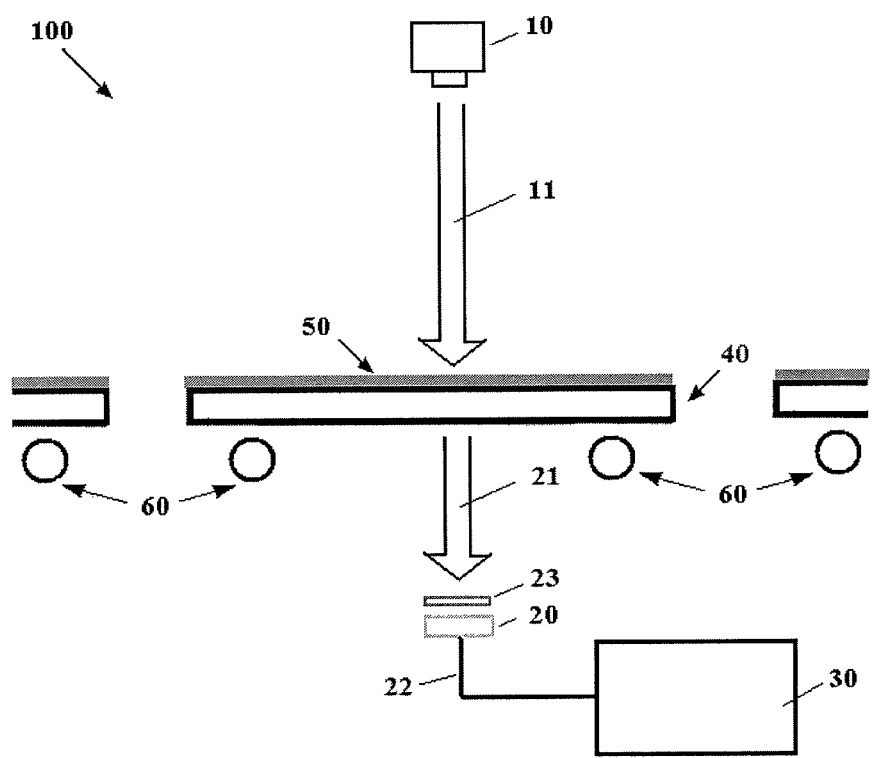
FIG. 2 is a diagram illustrating a metrology system.

Referring to FIG. 2, with a through measurement set-up, metrology system 100 can implement spectrophotometry technique for the investigation of the dielectric properties (complex refractive index or dielectric function) of thin films. Thereby, metrology system 100 can measure light absorption, diffuse or specular reflectance.

Metrology system 100 can use a monochromator (not shown in FIG. 2) containing a diffraction grating to produce the analytical spectrum. Metrology system 100 can also include measurement device and processing unit for infrared or lower frequency electromagnetic spectrum. Metrology system 100 can use a Fourier transform technique to acquire the spectral information quicker.

In some embodiments, metrology system 100 can quantitatively compares the fraction of light that passes through a reference sample and a test sample. Optical radiation 11 from optical source 10 can passed through a monochromator, which diffracts the light into a "rainbow" of wavelengths and outputs narrow bandwidths of this diffracted spectrum. Discrete frequencies can be transmitted through the test portion of semiconductor material 50. Then the intensity of the transmitted light 21 is measured with sensor 20, such as a photodiode or any other suitable light sensor. The transmittance value for this wavelength is then compared with the transmission through a reference sample (not shown in FIG. 2). The monochromator be placed in 30 to study the response on discrete frequencies on the analyzer side.

Figure 3:
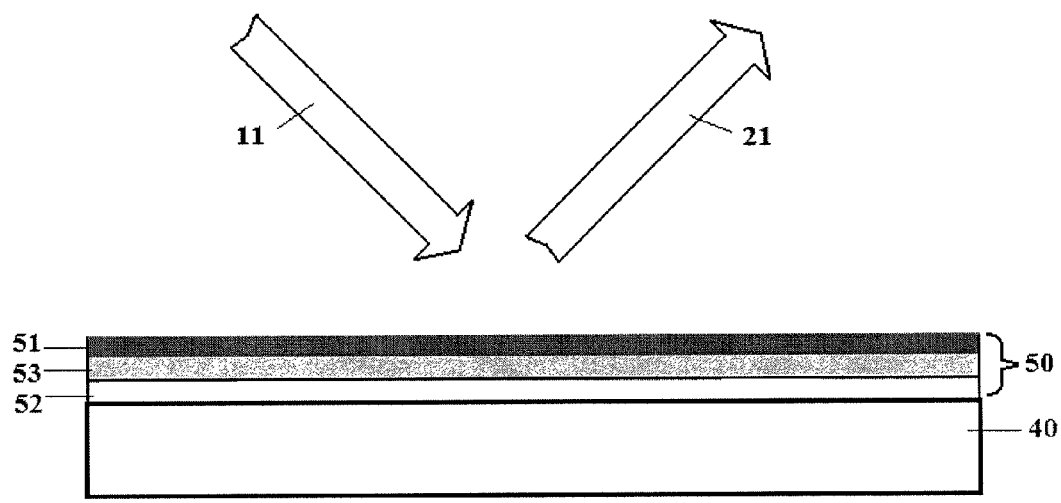
FIG. 3 is a diagram illustrating a metrology system.
Figure 4:
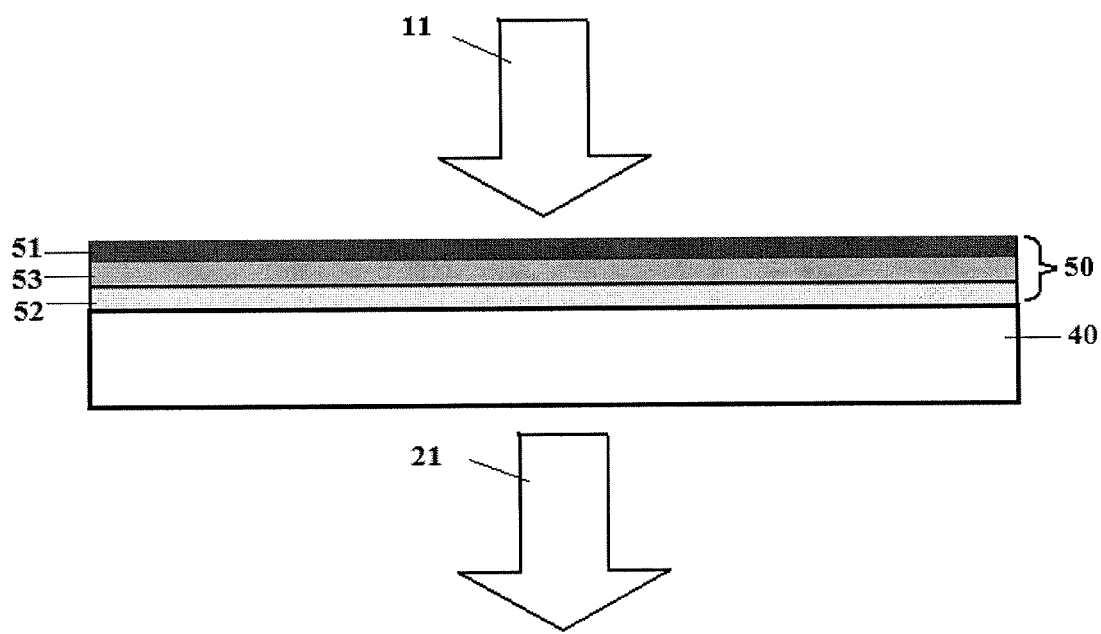
FIG. 4 is a diagram illustrating a metrology system.

Metrology system 100 can obtain information of multi-layer semiconductor material. Referring to FIGS. 3 and 4, in polycrystalline CdTe based photovoltaic module manufacturing, the main junction starts getting delineated during the semiconductor coating process—usually by controlling respective layer (CdS layer 52 and CdTe layer 51) thickness. In a subsequent halogen-mediated thermal process, semiconductor material 50 can be doped, the grain boundaries can be passivated and there is some intermixing of window layer (CdS) 52 and absorber layer (CdTe) 51. The inter-mixing results in CdS getting thinner and the formation of ternary ($CdS_xTe_{1-x}$) layer 53. The precise thickness of CdS layer 52 controls the optical response of the photovoltaic device especially in the blue region of the optical spectrum. The intermixing determines the junction quality (Jsc, FF, Roc and Voc) and possibly even the device stability.

In some embodiment, metrology system 100 can quantify the degree of this intermixing. While CdTe and CdS bandgaps are well defined, the intermixing can result in a compound whose band-gap can range from ~1.4 eV (lower than CdTe) to ~2.4 eV (CdS). The precise band-gap depends on the precise layer stoichiometry. The latter depends on inter-diffusion of the elements controlled by process variables. Metrology system 100 can measure the band-gap of CdS layer 52, CdTe layer 51 and intermixed layer 53 to predict the degree of intermixing and the final module performance characteristics.

Metrology system 100 can also be used to measure individual layer thickness (CdTe, CdS and the intermixed layer) or some total thickness. This and the intermixing information can be used to control deposition and diffusion anneal processes in real time. In another embodiment, the system can be used for CdTe—CdS photovoltaic device manufacturing process control.

The amount of intermixing and measured band-gaps for various layers also depends on specific impurities that may be added to a respective layer. Metrology system 100 can be used to quantify the impurity addition and efficacy of the process for doing the same.

The aforementioned information that is measured on the device stack being processed can be fed into a predictive model to estimate subsequent device parameters (e.g. Voc and Jsc). This would need inputs about some of the subsequent downstream processes like for e.g. Copper doping. Using an automated process control based set-up, the downstream process can even be adjusted to compensate for upstream process variation.

Figure 5:
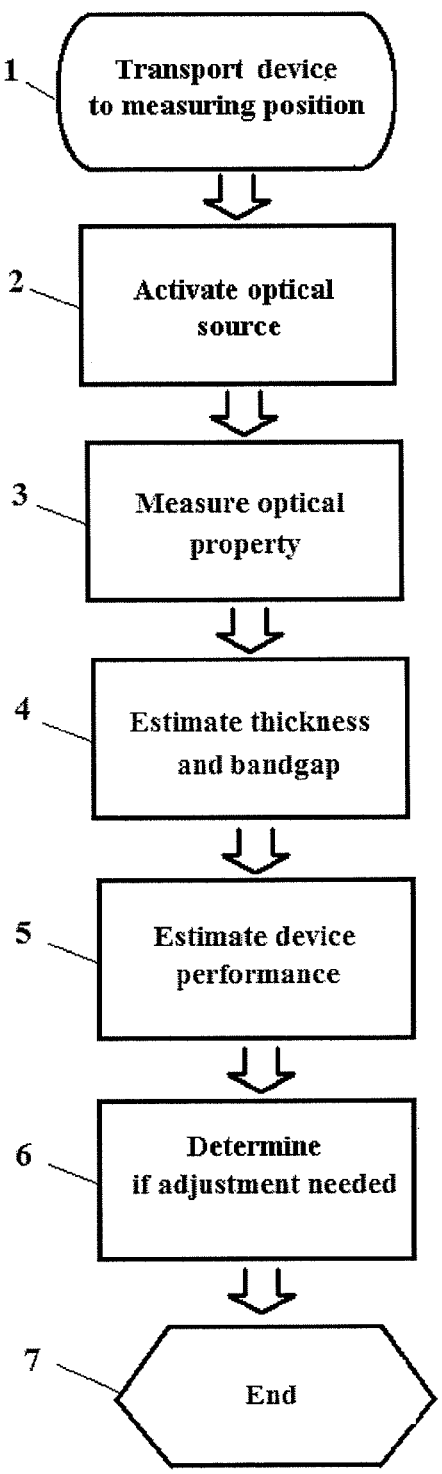
FIG. 5 is a flow chart illustrating an operation process of a metrology system.

Referring to FIG. 5, semiconductor device manufacturing process can include: step (1) transporting the device to a measuring position; step (2) activating the optical source; step (3) measuring the optical property of the deposited semiconductor material; step (4) estimating the thickness and band-gap of the deposited semiconductor material; step (5) estimating the device performance; step (6) determining if adjustments need to be made to former manufacturing process (e.g. deposition or annealing); and step (7) ending the measurement and transporting the device to the following manufacturing process. Metrology system can further include a feed-back control loop for adjusting the semiconductor film deposition and anneal process when it drifts from its purported baseline. In some embodiment, metrology system can adjust the measured location of the semiconductor material for spatially mapping a semiconductor material.

Predicting device behavior is well established in single-crystal based systems like Si and GaAs where the junction locations are precisely controlled by processes like Implant and Rapid Thermal Anneal. However, defining and controlling the junction location is a non-trivial problem in a polycrystalline device. This metrology system can measure a physical parameter critical to junction formation.

Therefore, the metrology system can have multiple applications in semiconductor device manufacturing process. For example, in photovoltaic device manufacture, the system can be used as:

1) Absorber purity monitor/semiconductor deposition process monitor: Doping the absorber with select impurities can result in conversion efficiency gains as high as half a percent provided the impurity concentration is within a certain window. Engineering (or scrap) and action limits on the dopant concentration can be defined from concentration optimization studies. An efficient way to ensure that absorber purity falls within the action limits is by setting up a metrology system downstream of the semiconductor deposition process. This metrology system should be able to measure the dopant concentration in real time and provide immediate feedback on the semiconductor deposition process performance. An example of an undesired situation is if the deposition process starts overdoping the absorber due to an excursion. One common cause for such excursions is hardware malfunction or breakdown.

Bandgap width in the CdTe—CdS device can change during anneal processes due to the intermixing of the layers. Band gap can also change in the bi-layer device described here, and other similar devices, by addition of certain impurities or alloying elements. Band gap energies are extracted from dark QE curves measured at zero bias.

In some embodiments, an optical band gap can also be extracted from spectroscopic measurements of the diffuse reflectance of the semiconductor by applying a Kubelka-Munk (KM) transformation. Under the assumption that the semiconductor band structure is parabolic and the semiconductor band gap is direct, the metrology system can correlate absorption coefficient, band gap energy and the diffuse reflectance. The result can be an estimation of band gap energy. The metrology system can be a reflectometer that will apply in real time a KM transform of the diffuse reflectance spectrum to extract absorber band gap. Band gap narrowing can negatively impact internal quantum efficiency. Furthermore, impurities and dopants in the absorber can significantly affect its microstructure and increase both bulk and interface recombination, resulting in sharp $V_{oc}$/FF drops.

2) Absorber thickness Monitor: The absorber thickness can be extracted from the wavelength period between consecutive interference fringes created in the optical cavity formed by air, the absorber and the layers beneath it.

3) Surface roughness or topography monitor: Using an appropriate range of optical wavelengths, surface roughness or a metric related to roughness can be measured based on the relative intensities of reflected and transmitted light.

4) Diffusion Anneal Process Monitor: The variation in band-gap can result from the change in temperature of the $CdCl_2$ Anneal process and the effect of adding Si to CdTe. The band-gap measured can be used to make conclusions about CdS—CdTe intermixing.

5) Automated Process Controller: As an automated process control system, the metrology system can operate in Feed-forward or Feed-back mode.

Figure 6:
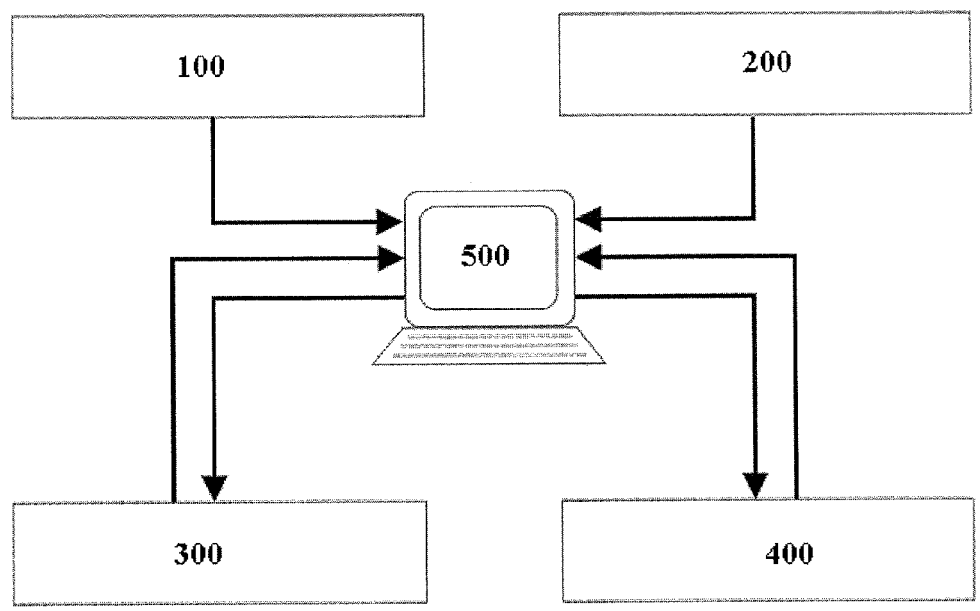
FIG. 6 is a diagram illustrating a metrology system and deposition system.

The Closed Loop Feedback Control System (FCS) is a computer integrated control system which utilizes multi-feedback loops from various solar panel submodule process sensors to actively affect the annealing oven and vapor deposition coater process control mechanisms. The manufacturing Key Process Indices include film thickness, roughness and band-gap. These values are derived from light transmission and reflectance characteristics of the submodule. Other KPIs can be obtained from sensors including but not limited to thermal line-scanners, spot pyrometers, hygrometers and thermocouples. These various input sources are wired into the control PC in which resides the control system. These inputs are used as product data that is both monitored and trended for control considerations. For example, referring to FIG. 6, a deposition system can include band edge detector 100, vapor deposition coater 200, annealing oven 300 and other suitable sensor 400, such as film thickness detector. The deposition process is monitored and controlled by control PC 500.

Figure 7:
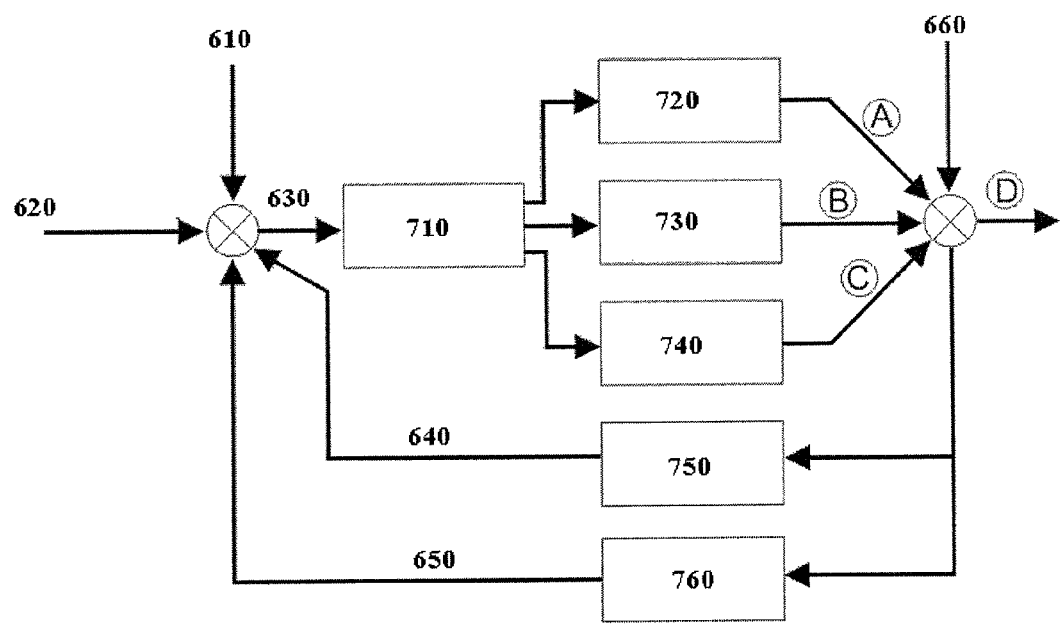
FIG. 7 is a diagram illustrating a metrology system control mechanism.

Referring to FIG. 7, there can be a control loop corresponding to each control mechanism: coater 720, annealing Oven Heater control and airflow control 730, and annealing oven linespeed control 740 (i.e., transport speed). The Heat loop can include secondary control loops for the upper and lower heating elements throughout the full length of the oven, with allowances for symmetry control Left and Right throughout the length of the oven as well. The control system utilizes adaptive control loops based on math modeling control 710 which resides on the Control PC (500 in FIG. 6). User screens allow for operator interface, networking, and complete process monitoring, control, and adjustment of the amount of control allowed to the Feedback Control System (FCS). SPC control may also be utilized for establishing acceptable limits of control and to alarm on out of control conditions. Mathematical models of the oven behavior and the Coater are integral to the FCS algorithm and are used to "temper" the amount and type of real-time control exerted by the system at any time as a function of process status. Input from sensors are stored in the FCS PC and through mathematical reduction are trended over long periods of time to establish when true shifts in operation occur. Spikes and impulse signals are observed, measured against known process status conditions, and filtered out if deemed purely an outlier condition. The math models take into account corresponding process reaction time constants, lag times, and deadtimes and the process inter-relationships in a coordinated multi-output aware fashion.

The purpose of this invention is to exert intelligent automatic control over the vapor deposition coater process 630 and the oven annealing process 610 so as to stabilize their respective output KPIs 620 from the perspective of the actual solar panel submodules piece to piece throughout long production runs regardless of external influences or long term instabilities, or excursions in the process equipment 660. It can also include band edge output 640 from band edge detector 750 and other sensor output 650 from other sensor 760. This results in improved process consistency and control—which implies better final product quality, improved yields, and allowance for increased throughput without destabilizing the oven process. Without such a control system, the photovoltaic module performance is influenced by uncontrolled external influences and process equipment variance that can include ambient temperatures, atmospheric conditions, heating element failure, asymmetry, and other inequalities, and gaps in production throughput. These gaps (or lack of submodules transiting the oven) disturb the equilibrium condition of the oven process allowing the oven to heat up to an undesired degree. By use of the FCS system, the effects of these external influences and process excursions are negated. Furthermore, the control system can include all the related factors, such as layer thickness from coater (A), heating effect from oven setpoints and airflow (B), submodule residency time from oven linespeed (C), and desired product performance characteristics (D).

In Feed-forward mode, the metrology system can provide information to downstream process tools of upstream excursion to make adjustments and corrections.

6) Device Performance Predictor: The modulation of device can result from $CdCl_2$ based diffusion anneal temperature. A system variable's accuracy can be contingent to precise matching of system performance and gauge used to measure the same. It is also often encumbered by the limitations of the manufacturing process e.g. gluing thermocouple to substrates that are passing through an oven, using a pyrometer on a window that is getting coated etc. The metrology system can provide the "missing-link" that obviates the need to directly correlate the device behavior to system metrics. Layer thickness and band gaps are physical and material characteristics that can be determined with greater degree of accuracy and the measurement process itself can be made independent of manufacturing process. In some embodiment, correlating device measurements to physical metrics in the device can result in automated process control.

In some embodiments, besides estimating the device performance based on the sensor measurement and the concomitant prediction of changes of the material properties, the metrology system can further adjust the semiconductor film deposition and anneal process when it drifts from its purported baseline with a feed-back control loop.

Figure 8:
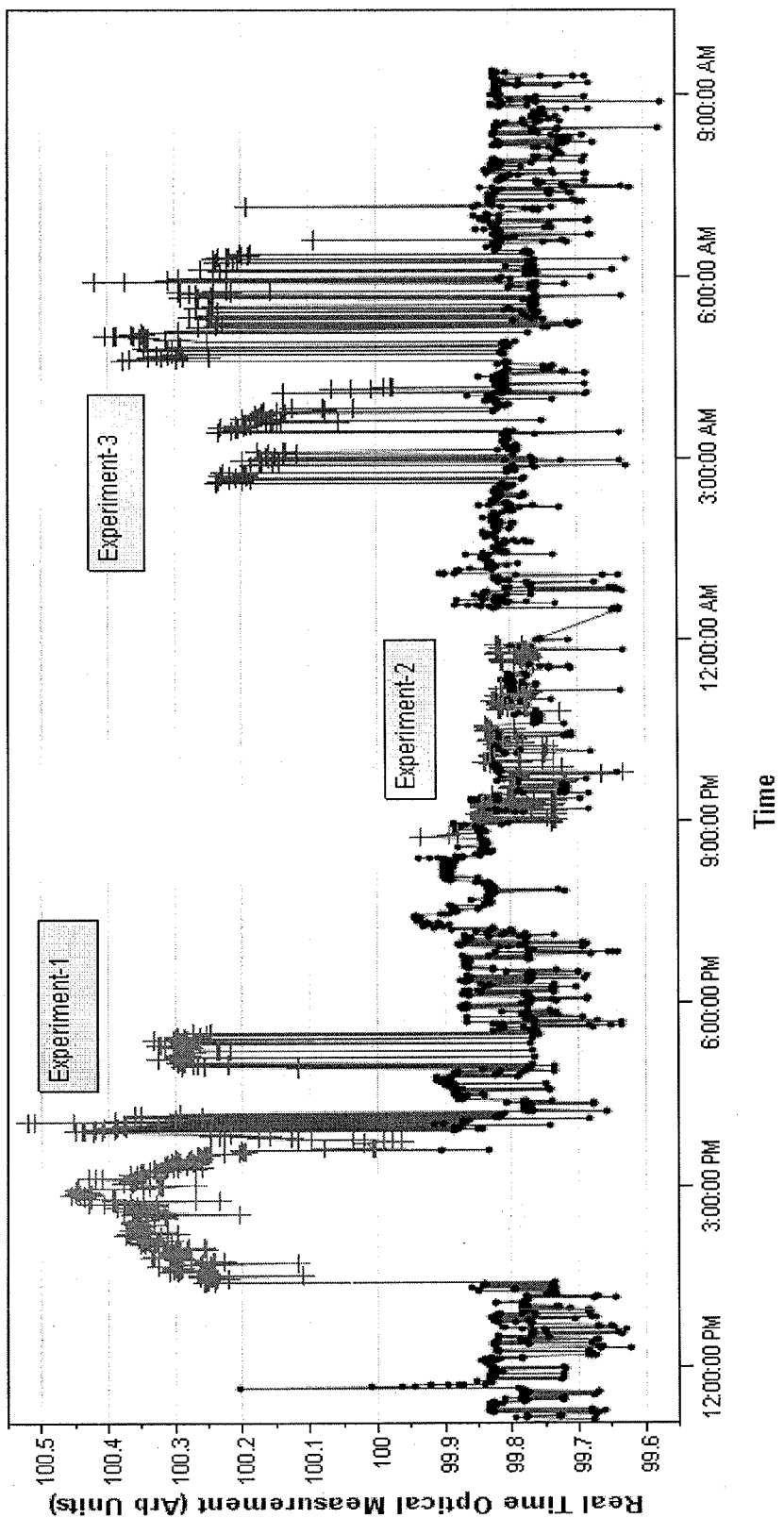
FIG. 8 is a diagram illustrating a real time optical measurement.
Figure 9:
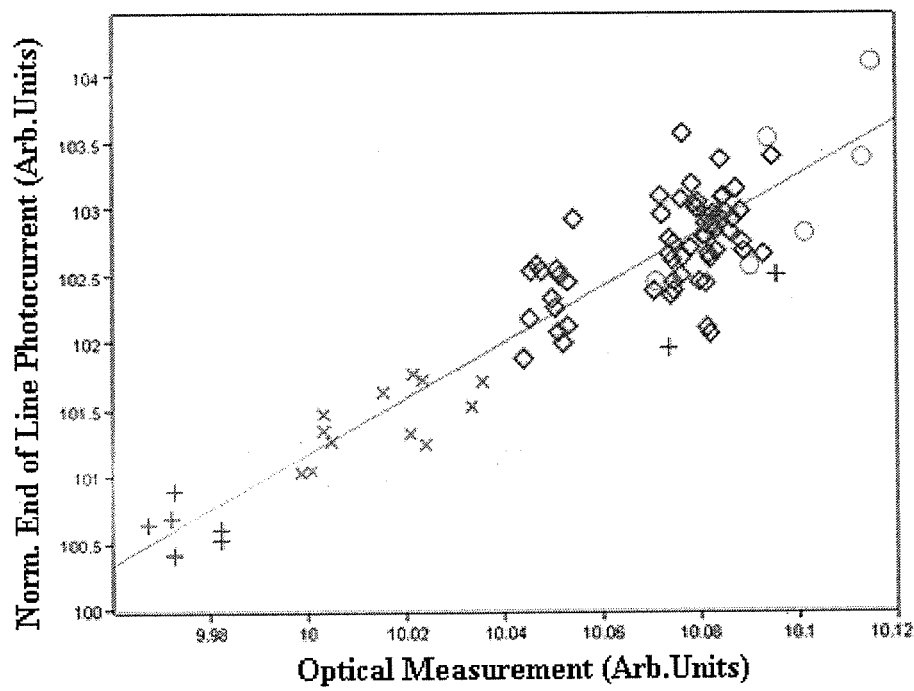
FIG. 9 is a diagram illustrating device parameters derived from optical measurements.
Figure 9:
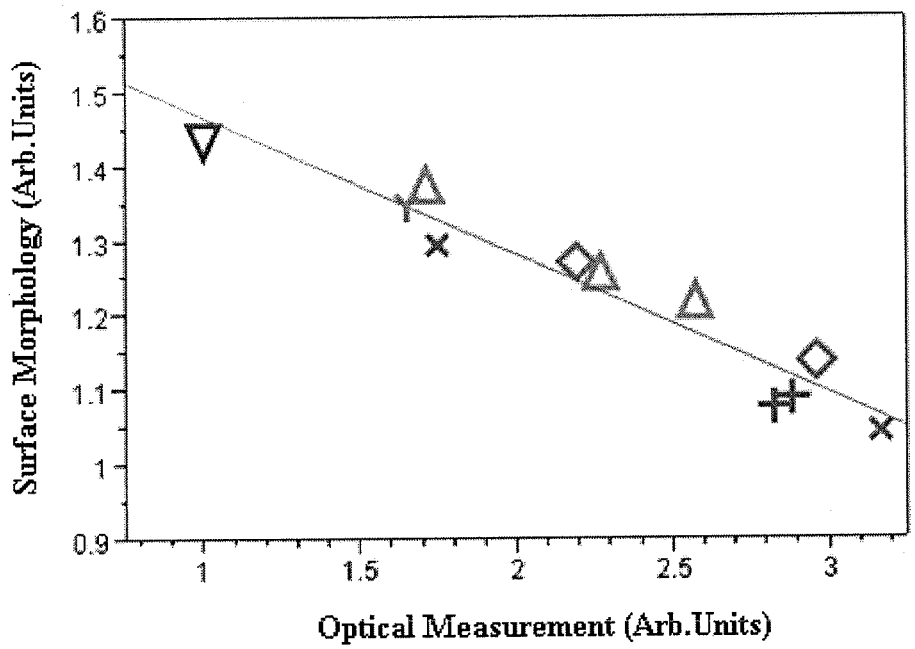

Referring to FIG. 8, optical measurement data can be collected in real time as plates are moving under the probe of the metrology system. Referring to FIG. 9, the optical measurement trend can be used to infer device metric, such as line photocurrent (A) and surface morphology (B). As shown in FIGS. 9 (A) and (B), a simple linear model can be used for simulation. The measurement of module physical metric can help estimating module performance and reliability. The measurement can further help estimating module performance and reliability. For example, device performance can be estimated based on the sensor measurement and a predictive model.

Figure 10:
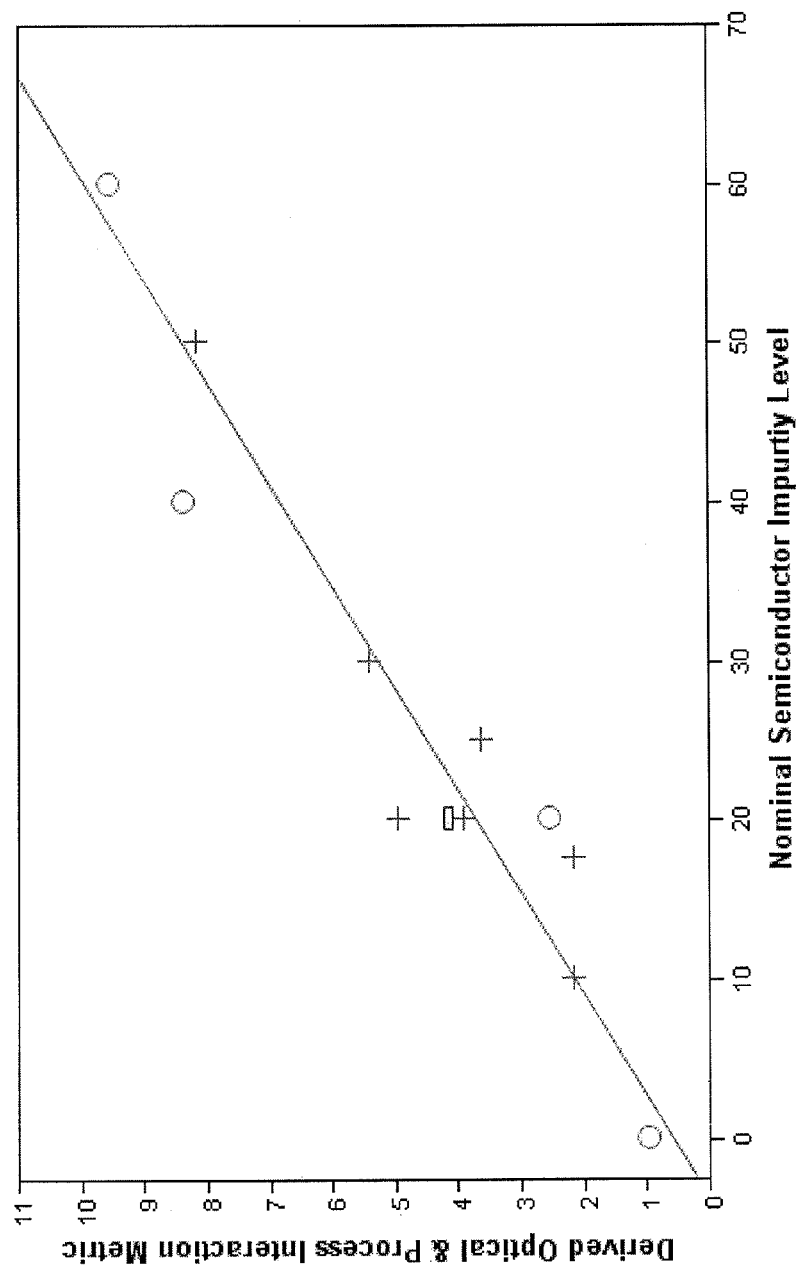
FIG. 10 is a diagram illustrating semiconductor quality derived from optical measurements.

Referring to FIG. 10, through suitable subsequent analysis, the semiconductor quality of photovoltaic modules can be gauged. For example, the semiconductor impurity level can be estimated using derived module physical metrics. Thereby, the semiconductor film deposition and anneal process can be adjusted when it drifts from its purported baseline with any suitable control mechanism, such as a feed-back control loop.

In some embodiments, the metrology system can also used in CIGS or CIS based photovoltaic devices where addition of Ga addition is typically used to control the band-gap. In some embodiments, the metrology system can used in any semiconductor device (such as opto-electronic device) manufacturing process where the device performance can be a result of optical properties like band-gap, physical ones like thickness and roughness can make use of this technology.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A metrology system for gauging characteristics of a photovoltaic semiconductor material formed on a substrate during a semiconductor film deposition and anneal process comprising:

an optical source for generating an optical radiation to illuminate a portion of the semiconductor material;

a sensor for measuring the absorption or reflection of the optical radiation in the semiconductor material; and a processing module for analyzing the sensor measurement to obtain the information of the band gap, absorption band-edge, thickness and surface roughness of the semiconductor material.

2. The metrology system of claim 1, wherein the substrate is transported on a conveyor.

3. The metrology system of any one of the preceding claims, wherein the metrology system is configured to measure the semiconductor material when the substrate is in motion.

4. The metrology system of claim 1 or claim 2, further comprising a feed-back control loop, wherein the system adjusts the semiconductor film deposition and anneal process when it drifts from its purported baseline.

5. The metrology system of claim 1 or claim 2, wherein the processing module provides an estimation of device performance based on the sensor measurement.

6. The metrology system of claim 1 or claim 2, further comprising a spectrophotometer.

7. The metrology system of claim 1 or claim 2, further comprising an ellipsometer.

8. The metrology system of claim 1 or claim 2, further comprising a quantum efficiency measurement setup, wherein the optical signal incident on the semiconductor material is converted to electrical signals to gauge the quantum efficiency of the semiconductor material.

9. The metrology system of claim 1 or claim 2, wherein the semiconductor material comprises cadmium telluride.

10. The metrology system of claim 1 or claim 2, wherein the semiconductor material comprises cadmium sulfide.

11. The metrology system of claim 1 or claim 2, further comprising an optical source that generates the probe beam that is incident on the sample being measured.

12. The metrology system of claim 1 or claim 2, further comprising an optical assembly to collect diffusion or specular reflection from the substrate.

13. The metrology system of claim 1 or claim 2, further comprising an optical assembly to collect the light transmitted through the semiconductor.

14. The metrology system of claim 1 or claim 2, wherein the sensor comprises a spectrometer to parse the light into component wavelengths.

15. The metrology system of claim 1 or claim 2, wherein the sensor comprises a photodiode or photo-multiplier to convert the optical signal to electrical signals for processing.

16. The metrology system of claim 1 or claim 2, wherein the semiconductor material comprises a bilayer of semiconductor material.

17. A method of gauging characteristics of a photovoltaic semiconductor material formed on a substrate during a semiconductor film deposition and anneal process comprising:

generating an optical radiation to illuminate a portion of the semiconductor material;

measuring the absorption or reflection of the optical radiation from the semiconductor material; and analyzing the measurement data to obtain the information on the optical band gap, absorption edge, surface roughness and thickness of the semiconductor material.

18. The method of claim 17, further comprising transporting the substrate on a conveyor.

19. The method of any one of claims 17-18, further comprising measuring the quantum efficiency of the semiconductor material.

20. The method of any one of claims 17-18, further comprising measuring the refractive index of the semiconductor material.

21. The method of any one of claims 17-18, further comprising correlating the optical properties of the semiconductor material to quantify the physical changes in the material, such as inter-diffusion.

22. The method of any one of claims 17-18, further comprising estimating the device performance based on the sensor measurement and the concomitant prediction of changes of the material properties.

23. The method of any one of claims 17-18, further comprising adjusting the semiconductor film deposition and anneal process when it drifts from its purported baseline with a feed-back control loop.

24. The metrology system of claim 10, wherein the semiconductor material comprises a mixed layer containing Cadmium Telluride and Cadmium Sulfide.

* * * * *